United States Patent [19]

Marsden et al.

[11] 4,038,456
[45] July 26, 1977

[54] AZIDO-SILANE COMPOSITIONS

[75] Inventors: James Glenn Marsden, Amawalk; Peter Joseph Orenski, Ossining, both of N.Y.

[73] Assignee: Union Carbide Corporation, New York, N.Y.

[21] Appl. No.: 626,041

[22] Filed: Oct. 28, 1975

Related U.S. Application Data

[62] Division of Ser. No. 483,365, June 26, 1974, Pat. No. 3,944,574.

[51] Int. Cl.$^2$ .............................................. B32B 9/00
[52] U.S. Cl. .................................. 428/391; 156/329; 428/429; 428/447; 428/450; 428/451; 428/448; 428/361
[58] Field of Search ............... 428/411, 429, 447, 450, 428/451, 391; 156/329; 427/387, 154

[56] References Cited

U.S. PATENT DOCUMENTS

| 3,507,829 | 4/1970 | Bostick et al. | 260/49 |
| 3,585,103 | 6/1971 | Thomson | 428/451 |
| 3,657,047 | 4/1972 | Breslow | 156/329 |
| 3,697,551 | 10/1972 | Thomson | 260/448.2 B |
| 3,705,911 | 12/1972 | Thomson | 260/29.2 M |
| 3,706,592 | 12/1972 | Thomson | 428/451 |
| 3,900,683 | 8/1975 | Haynes | 428/411 |

Primary Examiner—George F. Lesmes
Assistant Examiner—William R. Dixon, Jr.
Attorney, Agent, or Firm—Reynold J. Finnegan

[57] ABSTRACT

Azido-containing silane compositions of matter useful as coupling agents in the production of polymer composite articles.

15 Claims, No Drawings

AZIDO-SILANE COMPOSITIONS

This application is a divisional application of application Ser. No. 483,365, filed June 26, 1974 now U.S. Pat. No. 3,944,574.

BACKGROUND OF THE INVENTION

This invention relates to novel azido-silane compositions of matter and their uses.

While the prior art has heretofore disclosed azido containing silane compounds, e.g. U.S. Pat. Nos. 3,705,911 and 3,706,592, it has not been found to disclose or utilize the action of the azido-silane compositions of matter of this invention.

SUMMARY OF THE INVENTION

It has now been discovered that novel azidosilane compositions of matter can be prepared which have the advantage of being excellent coupling agents to promote bonding between inorganic substrates, such as siliceous, metallic or metal oxide materials and organic polymers.

Accordingly, it is an object of this invention to provide novel azido-silane compositions of matter. It is another object of this invention to provide composite articles comprising a filler or reinforcement base member and a polymeric matrix. Other objects and advantages of this invention will become readily apparent from the following description and appended claims.

More specifically, one aspect of this invention is directed to a solubilized azido-containing silane composition of matter produced by a process which comprises reacting in the presence of a solvent (a) an azido-containing carboxylic acid halide of the formula

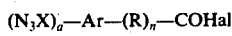

$(N_3X)_a—Ar—(R)_n—COHal$ wherein X is a radical selected from the group consisting of sulfonyl and formyl radicals, a is an integer of from 1 to 2, Ar is an aryl radical, R is a divalent alkylene radical having from 1 to 17 carbon atoms, wherein n has a value of 0 or 1; and Hal represents a halogen radical, with (b) an amino-containing silane having the formula

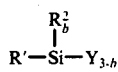

$R'—\underset{\underset{R^2_b}{|}}{Si}—Y_{3-b}$ wherein $R^2$ is a monovalent hydrocarbon radical, b has a value of 0 to 2, Y is a hydrolyzable group selected from the class consisting of alkoxy and aryloxy radicals and wherein R' is an organic radical directly bonded to the silicon atom of said silane through a carbon to silicon bond, said organic radical further containing at least one nitrogen atom which has a hydrogen atom bonded directly to it, said solvent being present in an amount sufficient to solubilize the azido-containing silane product of (a) and (b).

DESCRIPTION OF THE PREFERRED EMBODIMENTS

The azido-containing compounds, and/or methods for their production, employed in the instant invention are well known in the art, e.g. they can easily be prepared by halogenation of the corresponding azido containing carboxylic acid. As pointed out such compounds include carboxylic acid halides of the formula

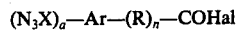

$(N_3X)_a—Ar—(R)_n—COHal$ wherein X is a radical selected from the group consisting of sulfonyl ($SO_2$) and formyl (COO) radicals, a is an integer of from 1 to 2, Ar is an aryl radical or a hydroxy-substituted aryl radical, preferably phenylene or hydroxy-phenylene, R is an alkylene radical having from 1 to 17 carbon atoms, n has a value of 0 or 1, preferably 0. The most preferred acids are those containing the azidosulfonyl radical. The most preferred azido-containing compound is

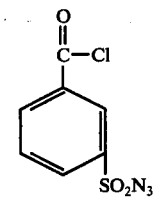

3-(azidosulfonyl) benzoyl chloride.

The amino-containing silane compounds, and/or methods for their preparation, employed in the instant invention are also well known in the art. As pointed out above, such silanes include those of the formula

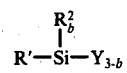

$R'—\underset{\underset{R^2_b}{|}}{Si}—Y_{3-b}$ wherein $R_2$ is a monovalent hydrocarbon radical having from 1 to 12 carbon atoms, b has a value of 0 to 2, preferably 0, Y is a member selected from the class consisting of alkoxy and aryloxy radicals having from 1 to 12 carbon atoms and wherein R' is an organic radical directly bonded to the silicon atom of said silane through a carbon to silicon bond, said organic radical further containing at least one nitrogen atom which has a hydrogen atom bonded directly to it.

Illustrative of R' are any organic radicals directly bonded to the silicon atom of said silane through a carbon to silicon bond, said organic radical further containing at least one nitrogen atom which has a hydrogen atom directly bonded to it (e.g. —NH). For instance among the more preferred organic radicals are those selected from the group consisting of aminoalkylene radicals such as amino methyl, betaaminomethyl, gamma-aminopropyl, delta-aminobutyl and the like; aminoaryl radicals such as aminophenyl and the like; alkylene polyamine radicals such as N-(betaaminoethyl)-gamma-aminopropyl, N-(beta-aminoethyl)-aminoethyl), N-(gamma-aminopropyl)-gamma-aminoisobutyl, N-beta-amino (polyethyleneimine) propyl, and the like; and polyazamide radicals such as taught in U.S. Pat. No. 3,746,738.

Most preferably R' represents an amino radical of the formula

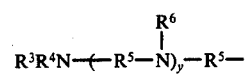

$R^3R^4N—(—R^5—\underset{\underset{R^6}{|}}{N})_y—R^5—$ wherein $R^3$, $R^4$ and $R^6$ individually represent a radical selected from the group consisting of hydrogen and a monovalent hydrocarbon radical having from 1 to 12 carbon atoms, at least one $R^3$, $R^4$ and $R^6$ group being hydrogen, and each $R^5$ group individually represents a divalent alkylene radical having from 1 to 10 carbon atoms, such as methylene, ethylene, propylene, butylene, hexylene, decylene, and the like, and $y$ is 0 or a positive integer, preferably $y$ has a value of 1 to 4. Preferably $R^5$ is a divalent alkylene radical having from 2 to 6 carbon atoms especially ethylene and propylene.

Illustrative monovalent hydrocarbon radicals that may be represented by $R^2$, $R^3$, $R^4$ and $R^6$ include such radicals as alkyl (e.g., methyl, ethyl, propyl, pentyl, dodecyl, and the like); cycloalkyl (such as cyclobutyl, cyclohexyl, and the like); aryl (such as phenyl, naphthyl, biphenyl, and the like); alkaryl (such as 4-methylphenyl, 2,4-diethylphenyl, and the like); arylalkyl (such as benzyl, beta-phenylethyl, and the like); and the like. Preferably, the monovalent hydrocarbon radical is a member selected from the group consisting of phenyl and lower alkyl radicals of 1 to 4 carbon atoms, especially a methyl radical.

Illustrative of Y groups are alkoxy radicals (such as methoxy, ethoxy, propoxy, isopropoxy, dodecyloxy, and the like), and aryloxy radicals (such as phenoxy, naphthyloxy, biphenyloxy, and the like). Preferably Y is a lower alkoxy radical of 1 to 4 carbon atoms, especially methoxy or ethoxy.

Silane compounds that can be employed in accordance with this invention include those described in U.S. Pat. Nos. 2,832,754; 2,942,019; 2,971,864; 3,321,350; and 3,746,738, the disclosure of which are incorporated herein by reference thereto. Specific examples of such amino-containing silane compounds include
aminomethyltrimethoxysilane,
gamma-aminopropyltrimethoxysilane,
gamma-methylaminopropyltrimethoxysilane,
gamma-aminopropyltriethoxysilane,
gamma-aminopropyltripropoxysilane,
gamma-aminopropylmethyldiethoxysilane,
gamma-aminopropylethyldiethoxysilane,
gamma-aminopropylphenyldietoxysilane,
gamma-amnoiosbutyltrimethoxysilane,
delta-aminobutyltriethoxysilane,
delta-aminobutylmethyldiethoxysilane,
beta-aminoethyltriethoxysilane,
epsilon-aminopentylphenyldibutoxysilane,
N-(beta-aminoethyl)-gammaaminopropyltrimethoxysilane,
N-(beta-dimethylaminoethyl)-gammaaminopropyltrimethoxysilane,
N-(beta-aminoethylaminoethyl)gamma-aminopropyltrimethoxysilane,
N-(gamma-amnopropyl)-gammaaminoisobutylmethyldiethoxysilane,
N-(beta-aminoethyl)-gamma-aminopropyltriethoxysilane,
1,4-aminophenyltrimethoxysilane,
beta-amino(polyethyleneimine) propyltrimthoxysilane,
silane containing polyazamides obtained e.g. by reacting a gamma-glycidoxypropyl-trimethoxysilane with a polyazamide polymer as taught in U.S. Pat. No. 3,746,738, and the like. The most preferred silanes are those wherein $R^3$, $R^4$, and $R^6$ are hydrogen atoms, especially N-beta-(aminoethyl)-gamma-aminopropyltrimethoxysilane.

The solvent employed by the instant invention in the production of the azido-containing silane compositions can be any non-aqueous solvent that will solubilize the product mixture of the azido-containing carboxylic acid halide and silane compounds used herein. Such solvents include conventional organic solvents such as alcohols (e.g. methanol, ethanol, propanol, and the like); ethers (e.g. diethylether, dipropylether, dimethoxyethane, and the like); ketones (e.g. acetone, methylethylketone, diethylketone, and the like); esters (e.g. methylacetate, ethylacetate, methylacetoacetate, ethylacetoacetate, methylpropionate, and the like); and the like. Preferably the solvent is one which is water soluble. The amount of solvent employed is not narrowly critical and obviously need only be at least that amount sufficient to solubilize the azido-containing silane composition of matter product and of course merely depends on the starting materials employed. Of course higher amounts of solvent can be employed if desired.

The azido-silane compositions of this invention are easily prepared as solvent solutions by mixing the solvent, the amino-containing silane compound and the azido-containing acid halide compound to form the solubilized product mixture of said compounds as witnessed by the clear product solution obtained. The azido-containing compound and amino-containing silane compound are normally employed in substantially equal molar quantities, that is to say from about 0.9 to about 1.1 moles of the azido-containing compound to about 1.1 to about 0.9 moles of amino-containing silane. The conditions of the mixing procedure to produce the azido-silane compositions of this invention are not narrowly critical. For instance the order of addition of ingredients may be varied and the mixing may be conducted at any suitable temperature and pressure. In general it is preferred to first form a solvent solution of the amino-containing silane compound and then slowly add the azido-containing compound, except when an alcoholic solvent is employed, then it is preferred to first form a solvent solution of the amino-containing silane compound and then add the azidocontaining compound. In general the mixing procedure is carried out at from 0° C to room temperature (20° C–30° C) and the reaction being exothermic allowed to proceed at temperatures up to the reflux point of the solvent. Of course, the reaction temperature is merely one of convenience and any suitable temperature can be employed. When an alcoholic solvent is employed however it is preferred to mix the ingredients and maintain the reaction temperature at −50° C to +10° C., preferably from −15° C to +5° C., so as to eliminate or at least minimize any possible side reactions which might occur. Of course the reaction is preferably conducted under atmospheric pressure although higher and lower pressures may be employed if desired. Moreover, if desired an azido-silane product solution may be first formed in one solvent and then the dried salt obtained therefrom added to a different solvent. Of course, it is obvious that mixtures of different solvents, different azido-containing compounds and/or different amino-containing silanes can be employed if desired. When the amino-containing silane compound employed is one which contains only one nitrogen atom, e.g. gamma-aminopropyltriethoxysilane, it is further desirable to employ a conventional acid acceptor such as a teriary amine, e.g. triethylamine, tripropylamine dimethylbenzylamine, dimethyloctylamine, pyridine, and the like, to remove the acid (e.g. HCl) byproduct from the reaction system. Moreover, if desired, an additional mole of any of the amino-containing silane compounds which contain only one nitrogen atom can be used as the acid acceptor. Such an acid acceptor is not required nor desired when the amino-containing silane compound employed is one which contains two nitrogen atoms, e.g. N-beta-(aminoethyl)-gamma-aminopropyltrimethoxysilane.

While not wishing to be bound by any precise structural configuration of the product mixture of the solubilized azido-silane compositions of this invention, for want of an illustration it is considered that, if desired, generic type structures may be given to the product mixtures of the solubilized azido-silane compositions of this invention. For example, the product mixture of 3-(azidosulfonyl) benzoyl chloride and gamma-aminopropyltriethyoxysilane might be represented by the formula

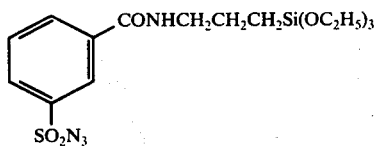

while the product mixture of 3-(azidosulfonyl) benzoylchloride and N-beta-(aminoethyl)-gamma-aminopropyltrimethoxysilane might be represented by the formula

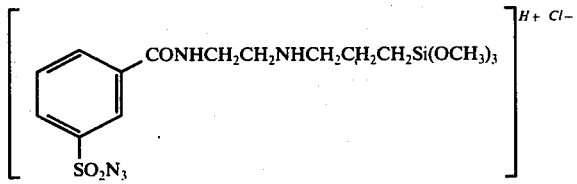

Of course it is to be understood that in addition to the above mentioned solubilized azido-containing silane composition, the instant invention also includes the azido-containing compounds obtained upon removal of the solvent. Clearly the solvent can be removed if desired, e.g. for the purpose of shipping or storage of a solid product, and the procedure employed for removal of the solvent is obviously not critical, any conventional method desired can be used, such as evaporation of the solvent, and the like.

Another aspect of this invention is directed to aqueous compositions of the solubilized azido-containing silane compositions of matter of this invention comprising from about 0.1 to about 20 parts by weight of the above defined solubilized azido-containing silane compositions of matter of this invention and from about 99.9 to about 80 parts by weight of water. Such aqueous compositions may be in the form of solutions, dispersions or emulsions depending upon the water solubility of the azido-containing silane product and the solvent used in producing same. For example it has been surprisingly discovered that the novel ionic azido-containing silane products produced by employing amino-containing silanes containing two nitrogen atoms (e.g. N-beta-aminoethyl)-gamma-aminopropyltrimethoxysilane) along with water-soluble solvents are easily soluble in water and form stable aqueous solutions. The preferred aqueous solutions of this invention are especially suitable for use as sizing and finishing agents in the fiber glass industry where water is overwhelmingly the preferred solvent. In forming the preferred aqueous solutions of this invention it is not necessary to remove the water-soluble solvent employed in production of the azido-silane product although such may be done if desired. Of course it is to be understood that since that aminocontaining silane compounds employed in this invention contain hyrolyzable groups (e.g. alkoxy radicals) the aqueous azido-silane product mixture compositions of this invention include and encompass the hydrolyzates and condensates of said azido-silane products. In addition it it obvious that the instant invention is also directed to the novel azido-containing compounds obtained upon removal of the water and any other solvent present in said aqueous compositions and such may be removed by any conventional manner.

The azido-silane compositions of matter of this invention can be used as coupling agents to enhance the adhesion of various substrates with a broad variety of polymers. The use of coupling agents to promote such bonding is well known in the art as witnessed for example by U.S. Pat. Nos. 2,832,754; 2,971,864; 3,258,477; 3,661,628; 3,671,562; 3,705,911; 3,706,592, and the like, the disclosures of which are incorporated herein by reference thereto.

More particularly the azido-silane compositions of matter of this invention have been found to be useful in promoting coupling and bonding between inorganic substrates, such as siliceous, metallic or metallic oxide materials and organic polymers.

Materials or substrates to which the organic polymers may be bonded include, siliceous materials such as glass, asbestos, sand, clay, talc, Wollastonite (calcium metasilicate), feldspar, concrete, ceramic materials, and the like; metals such as aluminum, copper, cadmium, chromium, magnesium, nickel, silver, tin, titanium, zinc, and the like; the alloys of such metals as brass, bronze, steel, and the like including metals which have been surface treated with phosphates, chromates, and the like; metal oxides such as aluminum oxide, iron oxides, lead oxides, titanium dioxide, zinc oxide and the like. If desired the organic polymers can even be bonded to other polymers through the azido-silane coupling agents. Of course it is understood that the particulr configuration of the inorganic substrate to which the organic polymer is bonded is not critical and that the inorganic materials can be in any various form such as sheets, plates, blocks, wires, cloth, fibers, filaments, particles, powders, and the like.

Oranic polymers that may be bonded to such inorganic substrates are well known in the art and include any of a wide variety of polymers mentioned in the patents cited above. Illustrative of some of the more preferred polymers are thermoplastic resins such as polyethylene, polypropylene, polystyrene, poly(vinyl chloride), polycarbonates, polyesters, nylon, polyacrylonitrile, and the like, as well as copolymers and terpolymers thereof; thermoset resins such as unsaturated polyesters, epoxies, phenolics, melamine, and the like; elastomers such as natural rubber, sytrene butadiene rubber, neoprene, ethylene propylene monomer rubber, ethylene propylene diene (e.g. hexadiene, ethylidene norborene, etc.) rubber, and the like. Of course like the base substrates the particular form of the organic polymer is not critical. The most preferred organic polymers are polyolefin thermoplastic resins, especially, polypropylene.

The procedures and conditions employed in bonding organic polymers and substrates through the use of coupling agents are well known in the art and any conventional method can be employed with the azido-silane compositions of this invention.

Thus as pointed out above an additional object of this invention can be described as an article of manufacture comprising a substrate selected from the group consisting of siliceous materials, metals, metal oxides and polymers coated with the novel azido-silane compositions of matter of this invention. Further articles of manufacture comprise an organic polymer bonded to a substrate selected from the group consisting of siliceous materials, metals, metal oxides and polymers through an azido-silane composition of matter of this invention. As pointed out above the most preferred substrate is a siliceous material, preferably glass and fiber glass while the preferred organic polymer is a polyolefin, especially polypropylene.

As pointed out the process employed in preparing the articles of manufacture of this invention is not critical and any conventional process can be employed. For example the material or substrate can be coated with an azido-silane composition of matter of this invention, allowed to dry and then coated with the organic polymer followed by curing the polymer on the coated substrate. Alternatively the azidosilane and the organic polymer can be deposited together on the substrate and then cured or the polymer can be first treated with the azido-silane compound and then coated on to the substrate and cured. Thus, there is provided a coupling agent at the interface of the substrate and organic polymer, said coupling agent being the azidosilane reaction products their hydrolyzates and condensates of this invention. The temperature at which the bonding reaction is carried out can be varied over a wide range depending upon the specific compounds employed. In general heat temperatures will normally be in the range of from about 100° C. to about 350° C., or higher. If desired the bonding between the substrate, azido-silane compositions and organic polymer may also be carried out by the use of ultra-violet light radiation, X-rays, and the like. The various amounts of compounds employed of course merely depend upon the azido-silane employed, the surface area to be covered, the organic polymer to be bonded to the material, and the like. Moreover, the method of coating the substrate is not critical and the azido-silane compositions of this invention can be sprayed, brushed, poured or rolled on to the surface of the material, and the like, or alternatively the material or substrate can be dipped into the solution of the azido-silane compositions of this invention. Thus it will be readily apparent to those skilled in the art that the azido-silane compositions of matter of this invention lend themselves to any conventional process where organic polymers are to be bonded to substrates such as siliceous materials, metals, metal oxides and other polymers.

The azido-silane compositions of matter of this invention have a number of advantages, for example they are very stable even under acidic conditions. Moreover, the physical properties and characteristics, such as flexural strength, tensile strength, falling dart impact, heat distortion temperature, and the like, of the resulting composites have been found to be considerably bettered as a result of the improved bonding between the organic polymer and substrates brought about by the action of the azidosilane compositions of this invention.

The following examples are illustrative of the present invention and are not to be regarded as limitative. It is to be understood that all of the parts, percentages and proportions referred to herein and in the appended claims are by weight unless otherwise indicated.

EXAMPLE 1

11.3 grams (50 milimoles) of 3-(azidosulfonyl) benzoic acid and 31 grams (261 milimoles) of thionyl chloride were added to a 200 ml. round bottom flask equipped with a magnetic stirrer, nitrogen sparge, reflux condenser and heating mantle. The mixture was stirred for 3 hours at 65° C. and then the excess thionyl chloride was stripped under vacuum. A 75 percent yield of 3-(azido-sulfonyl) benzoyl chloride was obtained and identified by spectroscopic analysis. Said benzoyl chloride was a straw-yellow liquid that slowly crystallized at room temperature and had a melting point of 41° C. and a refractive index of $N_D^{24.5} = 1.5751$.

EXAMPLE 2

23 grams (0.1 mole) of N-beta-(aminoethyl)-gammaaminopropyltrimethoxysilane dissolved in 30 grams of dimethoxy-ethane were added to a 200 ml. round bottom flask equipped with a magnetic stirrer, addition funnel, nitrogen sparge and cooling bath and the solution cooled to 0° C – 5° C. 25 grams (0.1 mole) of 3-(azidosulfonyl) benzoyl chloride in 18 grams of dimethoxyethane were added dropwise to the silane solution and the mixture stirred for 10 minutes at 0° C – 5° C. and then for one hour at room temperature. A quantitative yield of the desired ionic azido-silane product solution was obtained and spectroscopic analysis of the solutions showed formation of the desired azidosilane composition of matter. After stripping all the ether solvent the desired azido-silane reaction product was again identified by spectroscopic analysis.

Similar results may be obtained by employing other solvents such as acetone, methyl acetate and the like in place of the above dimethoxyethane ether solvent.

EXAMPLE 3

23 grams (0.1 mole) of N-beta-(aminoethyl)-gamma-amiopropyltrimethoxysilane dissolved in 60 ml. (48 grams) of methanol were added to a 200 ml. round-bottom flask equipped with a magnetic stirrer, addition funnel, nitrogen sparge and cooling bath and the solution cooled to at least about −5° C. 25 grams (0.1 mole) of 3-(azidosulfonyl) benzoyl chloride were added dropwise over fifteen minutes to the chilled silane solution. The mixture was stirred for one hour; the temperature rose to room temperature and there was obtained a reddish brown azido-silane reaction mixture in methanol. Spectroscopic analysis of the reaction product mixture showed formation of the desired ionic azido-silane composition of matter in an 80 – 85% yield together with a 15 – 20% by-product yield of the methyl ester of 3-(azidosulfonyl) benzoic acid.

EXAMPLE 4

A 6 percent water solution of the azido-silane dimethoxyethane ether product solution prepared as in Example 2 was used to size priscine glass fibers and the fibers then dried and chopped into ¼ inch lengths. The sized chopped strand was then mixed with polypropylene resin to give a blend containing 30 percent by weight of glass. The blend was injection molded at 480° F., (mold temperature 120° F, injection pressure 12,000 psi.) using a three ounce Van Dorn injection molder of 75 ton clamp pressure to yield test specimens of glass-reinforced polypropylene.

The test specimens showed a flexural strength of 14,800 psi., a tensile strength of 9,700 psi. and a heat-distortion temperature of 302° F. By comparison test specimens prepared from gamma-aminopropyltriethoxysilane coated chopped fiber glass strands and polypropylene showed a flexural strength of 9,900 psi., a tensile strength of 5,600 psi. and a heat-distortion temperature of 288° F., while test specimens prepared from commercial chopped fiber glass strands (specified for use in polypropylene) showed a flexural strength of 10,500 psi., a tensile strength of 6,600 psi. and a heat-distortion temperature of 298° F.

EXAMPLE 5

A 6 percent water solution of the azido-silane methanol product solution prepared as in Example 3 was used to size priscine glass fibers and the fibers then dried and chopped into ¼ inch lengths. The sized chopped strand was then mixed with modified polyphenylene oxide (Noryl) to give a blend containing 30 per cent by weight of glass. The blend was injection molded at 535° F. (mold temperature 210° F., injection pressure 20,000 psi.) using a three ounce VanDorn injection molder of 75 ton clamp pressure to yield test specimens of glass-reinforced modified polyphenylene oxide.

The test specimens showed a flexural strength of 22,600 psi., a tensile strength of 15,100 psi. and a heat-distortion temperature of 274° F. By comparison test specimens prepred from commercial chopped fiber glass strands (specified for use in modified polyphenylene oxide, e.g., Noryl) showed a flexural strength of 20,900 psi., a tensile strength of 13,800 psi. and a heat-distortion temperature of 277° F.

Various modifications and variations of this invention will be obvious to a worker skilled in the art and it is to be understood that such modifications and variations are to be included within the purview of this application and the spirit and scope of the appended claims.

What is claimed is:

1. An article of manufacture comprising a material selected from the group consisting of siliceous materials, metals, metal oxides and organic polymers coated with a solubilized azido-containing silane composition of matter produced by a process which comprises reacting in the presence of a non-aqueous solvent
   a. An azido-containing carboxylic acid halide of the formula $(N_3X)_a$—Ar—$(R)_n$—COHal wherein X is a radical selected from the group consisting of sulfonyl and formyl radicals, a is an integer of from 1 to 2, Ar is an aryl radical, R is a divalent akylene radical having from 1 to 17 atoms, wherein n has a value of 0 or 1; and Hal represents a halogen radical, with (b) an amino-containing silane having the formula

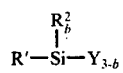

wherein $R^2$ is a monovalent hydrocarbon radical, b has a value of 0 to 2, Y is a hydrolyzable group selected from the class consisting of alkoxy and aryloxy radicals and wherein R' is an organic radical directly bonded to the silicon atom of said silane through a carbon to silicon bond, said organic radical further containing at least one nitrogen atom which has a hydrogen atom bonded directly to it, said solvent being present in an amount sufficient to solubilize the azido-containing silane product of (a) and (b).

2. An article of manufacture as defined in claim 1, wherein the material is glass.

3. An article of manufacture as defined in claim 2, wherein the material is fiber glass.

4. An article of manufacture comprising a material selected from the group consisting of siliceous materials, metals, metal oxides and organic polymers coated with an aqueous composition comprising from about 0.1 parts by weight to about 20 parts by weight of a solubilized azido-containing silane composition of matter as defined in claim 1, and from about 99.9 parts by weight to about 80 parts by weight of water.

5. An article of manufacture as defined in claim 4, whrein the material is glass.

6. An article of manufacture as defined in claim 5, wherein the material is fiber glass.

7. An article of manufacture comprising a material selected from the group consisting of siliceous materials, metals, metal oxides and organic polymers coated with an aqueous solution comprising from about 0.1 parts by weight to about 20 parts by weight of a solubilized azido-containing silane composition as defined in claim 1, wherein the non-aqueous solvent is selected from the group consisting of alcohols, ethers, ketones and esters; wherein X is a sulfonyl radical; a is 1; Ar is phenylene; x is 0; Hal is chlorine; b is 0; Y is a lower alkoxy radical having from 1 to 4 carbon atoms and R' is an amino radical of the formula

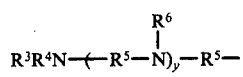

wherein $R^3$, $R^4$ and $R^6$ individually represent a radical selected from the group consisting of hydrogen and a methyl radical; y has a value of 1 to 4; and each $R^5$ group individually represents a divalent alkylene radical having from 2 to 6 carbon atoms; and from about 99.9 parts by weight to about 80 parts by weight of water.

8. An article of manufacture as defined in claim 7, wherein the material is glass.

9. An article of manufacture as defined in claim 8, wherein the material is fiber glass.

10. An article of manufacture as defined in claim 7, wherein $R^3$, $R^4$ and $R^6$ are hydrogen atoms.

11. An article of manufacture as defined in claim 10, wherein the azido-containing compound is 3-(azidosulfonyl) benzoyl chloride and the amino-containing silane is N-beta-(aminoethyl)-gamma-aminopropyltrimethoxy silane.

12. An article of manufacture comprising an organic polymer bonded to a substrate through a coupling agent, said coupling agent being the reaction product of an azido-containing carboxylic acid halide of the formula $(N_3X)_a$—Ar—$(R)_n$—COHal wherein X is a radical selected from the group consisting of sulfonyl and formyl radicals, a is an integer of from 1 to 2, Ar is an aryl radical, R is a divalent alkylene radical having from 1 to 17 carbon atoms, wherein $n$ has a value of 0 or 1; and Hal represents a halogen radical, with an amino-containing silane having the formula

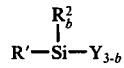

wherein $R^2$ is a monovalent hydrocarbon radical, $b$ has a value of 0 to 2, Y is a hydrolyzable group selected from the class consisting of alkoxy and aryloxy radicals and wherein R' is an organic radical directly bonded to the silicon atom of said silane through a carbon to silicon bond, said organic radical further containing at least one nitrogen atom which has a hydrogen atom bonded directly to it, their hydrolyzates and the condensates thereof, said substrate being selected from the group consisting of siliceous materials, metals, metal oxides, and other organic polymers.

13. An article of manufacture as defined in claim 12, wherein the substrate is glass.

14. An article of manufacture as defined in claim 12, wherein the organic polymer is a polyolefin.

15. An article of manufacture as defined in claim 3, wherein the substrate is fiber glass and the organic polymer is polypropylene.

* * * * *

UNITED STATES PATENT AND TRADEMARK OFFICE
CERTIFICATE OF CORRECTION

PATENT NO. : 4,038,456
DATED : July 26, 1977
INVENTOR(S) : James Glenn Marsden et al.

It is certified that error appears in the above-identified patent and that said Letters Patent are hereby corrected as shown below:

Column 12, line 12, the number "3" should read -- 13 --.

*Signed and Sealed this*

*Fifth* Day of *June 1979*

[SEAL]

Attest:

RUTH C. MASON
*Attesting Officer*

DONALD W. BANNER
*Commissioner of Patents and Trademarks*